United States Patent [19]

Wityak et al.

[11] Patent Number: 5,446,056
[45] Date of Patent: Aug. 29, 1995

[54] ISOXAZOLINE COMPOUNDS USEFUL AS FIBRINOGEN RECEPTOR ANTAGONISTS

[75] Inventors: John Wityak, West Grove, Pa.; Thais M. Sielecki-Dzurdz, Newark, Del.

[73] Assignee: The Du Pont Merck Pharmaceutical Company, Wilmington, Del.

[21] Appl. No.: 304,614

[22] Filed: Sep. 12, 1994

Related U.S. Application Data

[63] Continuation-in-part of Ser. No. 157,851, Nov. 24, 1993, abandoned.

[51] Int. Cl.$^6$ .................... A61K 31/44; A61K 31/42; C07D 261/04; C07D 413/12
[52] U.S. Cl. .................... 514/340; 514/326; 514/236.8; 514/378; 544/137; 546/275; 548/240
[58] Field of Search ............. 548/240; 514/378, 340, 514/326; 544/137; 546/275, 209

[56] References Cited

U.S. PATENT DOCUMENTS

| | | | |
|---|---|---|---|
| 5,039,805 | 8/1991 | Alig et al. | 546/224 |
| 5,187,157 | 2/1993 | Kettner et al. | 514/18 |

FOREIGN PATENT DOCUMENTS

| | | | |
|---|---|---|---|
| 2008311 | 7/1990 | Canada | 546/229 |
| 2061661 | 9/1992 | Canada | 546/304 |
| 2074685 | 1/1993 | Canada | 548/240 |
| 2093770 | 10/1993 | Canada | 548/557 |
| 381033 | 8/1990 | European Pat. Off. | 546/275 |
| 445796 | 9/1991 | European Pat. Off. | 546/229 |
| 478328 | 4/1992 | European Pat. Off. | 546/229 |
| 478362 | 4/1992 | European Pat. Off. | 546/229 |
| 478363 | 4/1992 | European Pat. Off. | 546/229 |
| 512829 | 11/1992 | European Pat. Off. | 546/201 |
| 0512831 | 11/1992 | European Pat. Off. | 548/566 |

OTHER PUBLICATIONS

Phillips et al. *Cell* (1991) 65, 359–362, GP116-111a: The Responsive Integrin.
Hartman et al. *J Med Chem* (1992) 35 4640–4642, Non-Peptide . . . Exosite Inhibitors.
Alig et al. *J Med Chem* (1992) 35 4393–4407, Low Molecular . . . Antagonists.

*Primary Examiner*—Joseph K. McKane
*Attorney, Agent, or Firm*—Blair Q. Ferguson

[57] ABSTRACT

This invention relates to novel isoxazolines which are useful as antagonists of the platelet glycoprotein IIb-/IIIa fibrinogen receptor complex, to pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

20 Claims, No Drawings

ISOXAZOLINE COMPOUNDS USEFUL AS FIBRINOGEN RECEPTOR ANTAGONISTS

CROSS REFERENCE TO EARLIER FILED APPLICATION

This application is a continuation-in-part of U.S. patent application Ser. No. 08/157,851, filed Nov. 24, 1993, now abandoned. The disclosure of this earlier filed application is hereby incorporated herein by reference.

FIELD OF THE INVENTION

This invention relates to novel isoxazolines which are useful as antagonists of the platelet glycoprotein IIb/IIIa fibrinogen receptor complex, to pharmaceutical compositions containing such compounds, processes for preparing such compounds, and to methods of using these compounds, alone or in combination with other therapeutic agents, for the inhibition of platelet aggregation, as thrombolytics, and/or for the treatment of thromboembolic disorders.

BACKGROUND OF THE INVENTION

Hemostasis is the normal physiological process in which bleeding from an injured blood vessel is arrested. It is a dynamic and complex process in which platelets play a key role. Within seconds of vessel injury, resting platelets become activated and are bound to the exposed matrix of the injured area by a phenomenon called platelet adhesion. Activated platelets also bind to each other in a process called platelet aggregation to form a platelet plug. The platelet plug can stop bleeding quickly, but it must be reinforced by fibrin for long-term effectiveness, until the vessel injury can be permanently repaired.

Thrombosis may be regarded as the pathological condition wherein improper activity of the hemostatic mechanism results in intravascular thrombus formation. Activation of platelets and the resulting platelet aggregation and platelet factor secretion has been associated with a variety of pathophysiological conditions including cardiovascular and cerebrovascular thromboembolic disorders, for example, the thromboembolic disorders associated with unstable angina, myocardial infarction, transient ischemic attack, stroke, atherosclerosis and diabetes. The contribution of platelets to these disease processes stems from their ability to form aggregates, or platelet thrombi, especially in the arterial wall following injury.

Platelets are activated by a wide variety of agonists resulting in platelet shape change, secretion of granular contents and aggregation. Aggregation of platelets serves to further focus clot formation by concentrating activated clotting factors at the site of injury. Several endogenous agonists including adenosine diphosphate (ADP), serotonin, arachidonic acid, thrombin, and collagen, have been identified. Because of the involvement of several endogenous agonists in activating platelet function and aggregation, an inhibitor which acts against all agonists would represent a more efficacious antiplatelet agent than currently available antiplatelet drugs, which are agonist-specific.

Current antiplatelet drugs are effective against only one type of agonist; these include aspirin, which acts against arachidonic acid; ticlopidine, which acts against ADP; thromboxane A2 synthetase inhibitors or receptor antagonists, which act against thromboxane A2; and hirudin, which acts against thrombin.

Recently, a common pathway for all known agonists has been identified, namely platelet glycoprotein IIb/IIIa complex (GPIIb/IIIa), which is the membrane protein mediating platelet aggregation. A recent review of GPIIb/IIIa is provided by Phillips et al. *Cell* (1991) 65, 359-362. The development of a GPIIb/IIIa antagonist represents a promising new approach for antiplatelet therapy.

GPIIb/IIIa does not bind soluble proteins on unstimulated platelets, but GPIIb/IIIa in activated platelets is known to bind four soluble adhesive proteins, namely fibrinogen, von Willebrand factor, fibronectin, and vitronectin. The binding of fibrinogen and von Willebrand factor to GPIIb/IIIa causes platelets to aggregate. The binding of fibrinogen is mediated in part by the Arg-Gly-Asp (RGD) recognition sequence which is common to the adhesive proteins that bind GPIIb/IIIa.

Several RGD-peptidomimetic compounds have been reported which block fibrinogen binding and prevent the formation of platelet thrombi.

European Patent Application Publication Number 478363 relates to compounds having the general formula:

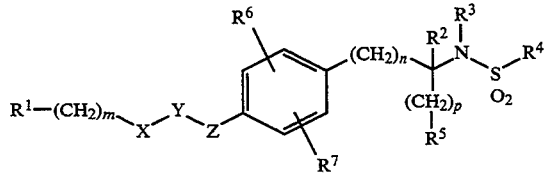

European Patent Application Publication Number 478328 relates to compounds having the general formula:

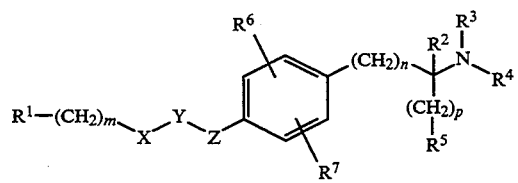

European Patent Application Publication Number 525629 (corresponds to Canadian Patent Application Publication Number 2,074,685) discloses compounds having the general formula:

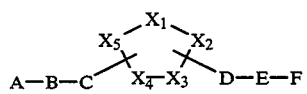

PCT Patent Application 9307867 relates to compounds having the general formula:

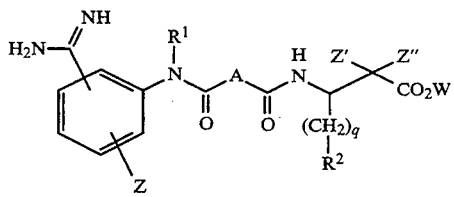

European Patent Application Publication Number 4512831 relates to compounds having the general formula:

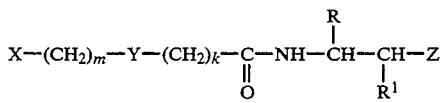

SUMMARY OF THE INVENTION

This invention provides novel compounds of Formula I (described below) which are useful as antagonists of the platelet glycoprotein IIb/IIIa complex. The compounds of the present invention inhibit the binding of fibrinogen to platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

The present invention also includes methods of treating thromboembolic disorders by administering a compound of Formula I in combination with one or more second therapeutic agents selected from: anti-coagulants such as warfarin or heparin; anti-platelet agents such as aspirin, piroxicam or ticlopidine; thrombin inhibitors such as boropeptides, hirudin or argatroban; or thrombolytic agents such as tissue plasminogen activator, anistreplase, urokinase or streptokinase; or combinations thereof.

Also included in the present invention are pharmaceutical kits comprising one or more containers containing pharmaceutical dosage units comprising a compound of Formula I, for the treatment of thromboembolic disorders.

DETAILED DESCRIPTION OF THE INVENTION

This invention provides compounds of Formula I (described below) which are useful as antagonists of the platelet glycoprotein IIb/IIIa complex. The compounds of the present invention inhibit the binding of fibrinogen to the platelet glycoprotein IIb/IIIa complex and inhibit the aggregation of platelets. The present invention also includes pharmaceutical compositions containing such compounds of Formula I, and methods of using such compounds for the inhibition of platelet aggregation, as thrombolytics, and/or for the treatment of thromboembolic disorders.

This invention provides compounds, or pharmaceutically acceptable salt or prodrug forms thereof, of the Formula I:

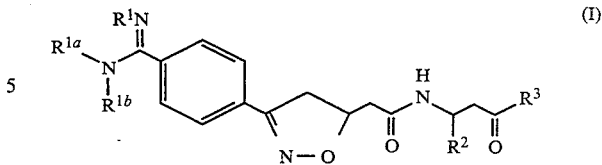

wherein:

$R^1$ and $R^{1a}$ are independently selected from: H, $OR^{4a}$, $C_1$–$C_{10}$ alkyl, $C_2$–$C_6$ alkenyl, $C_3$–$C_{11}$ cycloalkyl, $C_4$–$C_{11}$ cycloalkylalkyl, $C_6$–$C_{10}$ aryl, $C_7$–$C_{14}$ arylalkyl, heteroaryl($C_1$–$C_{10}$)alkyl, $C_2$–$C_7$ alkylcarbonyl, $C_6$–$C_{10}$ arylcarbonyl, $C_2$–$C_{10}$ alkoxycarbonyl, $C_4$–$C_{11}$ cycloalkoxycarbonyl, $C_7$–$C_{14}$ bicycloalkoxycarbonyl, aryloxycarbonyl, aryl($C_1$–$C_{10}$ alkoxy)carbonyl, or heteroarylcarbonyl;

with the proviso that only one of $R^1$ or $R^{1a}$ can be $OR^{4a}$, $C_2$–$C_7$ alkylcarbonyl, arylcarbonyl, $C_2$–$C_{10}$ alkoxycarbonyl, $C_4$–$C_{11}$ cycloalkoxycarbonyl, $C_7$–$C_{14}$ bicycloalkoxycarbonyl, aryloxycarbonyl, aryl($C_1$–$C_{10}$ alkoxy)carbonyl, or heteroarylcarbonyl;

$R^{1b}$ is H, $C_1$–$C_{10}$ alkyl, $C_2$–$C_6$ alkenyl, $C_3$–$C_{11}$ cycloalkyl, OH, $OR^4$, $C_4$–$C_{11}$ cycloalkylalkyl, $C_6$–$C_{10}$ aryl, $C_7$–$C_{14}$ arylalkyl, or heteroaryl($C_1$–$C_{10}$)alkyl;

alternatively, $R^{1a}$ and $R^{1b}$ can be taken together with the nitrogen atom to which they are attached to form a 5–7 membered heterocyclic ring optionally containing 1 additional heteroatom selected from O, N or S, said heterocyclic ring being substituted with 0–2 $R^4$;

alternatively, $R^1$ and $R^{1a}$ can join to form a saturated or unsaturated carbon chain of 2–4 carbons thereby forming a 5–7 membered heterocyclic ring, said heterocyclic ring being substituted with 0–2 $R^4$;

$R^2$ is selected from H or $CH_3$;

$R^3$ is selected from: hydroxy, $C_1$ to $C_{10}$ alkyloxy, $C_3$ to $C_{11}$ cycloalkyloxy, $C_6$ to $C_{10}$ aryloxy, $C_7$ to $C_{14}$ arylalkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonyloxy, $C_7$ to $C_{11}$ aryloxycarbonyloxy, $C_8$ to $C_{12}$ aryloxycarbonyloxyalkyloxy, $C_8$ to $C_{14}$ arylcarbonyloxyalkyloxy, $C_5$ to $C_{10}$ alkoxyalkylcarbonyloxyalkyloxy, $C_5$ to $C_{10}$ (5-alkyl-1,3-dioxacyclopenten-2-one-yl)methyloxy, $C_{10}$ to $C_{14}$ (5-aryl-1,3-dioxacyclopenten-2-one-yl)methyloxy, $C_5$–$C_{10}$ alkyldioxolenonylmethoxy, aryldioxolenonylmethoxy, N-morpholinoethoxy, or $(R^5)_2N$–$C_1$–$C_{10}$ alkyloxy;

$R^4$, when a substituent on carbon, is independently selected from: H, $C_1$–$C_4$ alkyl, aryl, or aryl($C_1$–$C_{10}$ alkyl)-;

when $R^4$ is attached to a saturated carbon atom, it may also be =O or =S;

$R^4$, when a substituent on nitrogen, is independently selected from:

H, $C_1$–$C_4$ alkyl, aryl($C_1$–$C_{10}$ alkyl)-, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl(-$C_2$–$C_{10}$ alkenyl)sulfonyl, heteroarylsulfonyl, $C_2$–$C_4$ alkenyl, $C_4$–$C_7$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl, or aryl($C_1$-$C_{10}$ alkoxy)carbonyl;

$R^4$, when a substituent on sulfur, may be =O;

$R^{4a}$ is selected from: H, $C_1$-$C_6$ alkyl, $C_6$-$C_{10}$ aryl, $C_7$-$C_{14}$ arylalkyl, heteroaryl, heteroaryl($C_1$-$C_{10}$)alkyl, $C_3$-$C_7$ cycloalkyl, $C_4$-$C_{11}$ cycloalkylalkyl, arylcarbonyl, $C_1$-$C_{10}$ alkylcarbonyl or aryl($C_1$-$C_4$)alkylcarbonyl;

$R^5$ is independently selected from: H, $OR^{4a}$, $C_1$-$C_{10}$ alkyl, $C_2$-$C_6$ alkenyl, $C_3$-$C_{11}$ cycloalkyl, $C_4$-$C_{11}$ cycloalkylalkyl, $C_6$-$C_{10}$ aryl, $C_7$-$C_{14}$ arylalkyl, heteroaryl($C_1$-$C_{10}$)alkyl, $C_2$-$C_7$ alkylcarbonyl, $C_6$-$C_{10}$ arylcarbonyl, $C_2$-$C_{10}$ alkoxycarbonyl, $C_4$-$C_{11}$ cycloalkoxycarbonyl, $C_7$-$C_{14}$ bicycloalkoxycarbonyl, aryloxycarbonyl, aryl($C_1$-$C_{10}$ alkoxy)carbonyl, or heteroarylcarbonyl;

alternatively, two $R^5$ groups can be taken together with the nitrogen atom to which they are attached to form a 5-7 membered heterocyclic ring optionally containing 1 additional heteroatom selected from O, N or S, said heterocyclic ring being substituted with 0-2 $R^4$.

Preferred compounds of this invention are compounds, or pharmaceutically acceptable salt or prodrug forms thereof, of the Formula I wherein: $R^1$ is selected from H, aryl($C_1$-$C_{10}$ alkoxy)carbonyl, or $C_2$-$C_{10}$ alkoxycarbonyl;

$R^{1a}$ is selected from: H, $OR^{4a}$, $C_1$-$C_6$ alkyl, $C_2$-$C_6$ alkenyl, $C_3$-$C_{11}$ cycloalkyl, $C_4$-$C_{11}$ cycloalkylalkyl, aryl, aryl-$C_1$-$C_{10}$ alkyl, heteroaryl($C_1$-$C_{10}$)alkyl, $C_2$-$C_7$ alkylcarbonyl, arylcarbonyl, $C_2$-$C_{10}$ alkoxycarbonyl, $C_4$-$C_{11}$ cycloalkoxycarbonyl, $C_7$-$C_{14}$ bicycloalkoxycarbonyl, aryloxycarbonyl, aryl($C_1$-$C_{10}$ alkoxy)carbonyl, or heteroarylcarbonyl;

$R^{1b}$ is H;

alternately, $R^{1a}$ and $R^{1b}$ can be taken together with the nitrogen atom to which they are attached to form a 5-6 membered heterocyclic ring optionally containing 1 additional heteroatom selected from O, N or S, said heterocyclic ring being substituted with 0-2 $R^4$;

$R^2$ is selected from: H or $CH_3$;

$R^3$ is selected from: hydroxy, $C_1$-$C_{10}$ alkyloxy, aryloxy, aryl-$C_1$-$C_{10}$ alkoxy, $C_3$-$C_{10}$ alkyloxycarbonyloxyalkoxy, $C_8$-$C_{14}$ arylcarbonyloxyalkoxy, $C_5$-$C_{10}$ alkyldioxolenonylmethoxy, aryldioxolenonylmethoxy, $C_5$-$C_{10}$ cycloalkoxycarbonyloxyalkoxy, $C_5$-$C_{10}$ alkyloxyalkylcarbonyloxyalkyloxy, or N-morpholinoethoxy;

$R^4$, when a substituent on carbon, is independently selected from: H, $C_1$-$C_4$ alkyl, aryl, or aryl($C_1$-$C_{10}$ alkyl)-, or when $R^4$ is attached to a saturated carbon atom it may be =O;

$R^4$, when a substituent on nitrogen, is independently selected from:

H, $C_1$-$C_4$ alkyl, aryl($C_1$-$C_{10}$ alkyl)-, $C_1$-$C_{10}$ alkoxycarbonyl, $C_1$-$C_{10}$ alkylcarbonyl, $C_4$-$C_7$ cycloalkylalkyl, $C_7$-$C_{11}$ arylcarbonyl, $C_7$-$C_{11}$ aryloxycarbonyl, or aryl($C_1$-$C_{10}$ alkoxy)carbonyl;

$R^{4a}$ is selected from: H, $C_1$-$C_6$ alkyl, $C_7$-$C_{14}$ arylalkyl, heteroaryl($C_1$-$C_{10}$)alkyl, $C_3$-$C_7$ cycloalkyl, $C_4$-$C_{11}$ cycloalkylalkyl, arylcarbonyl, $C_1$-$C_{10}$ alkylcarbonyl or aryl($C_1$-$C_4$)alkylcarbonyl.

Further preferred compounds of this invention are those compounds of Formula I wherein:

$R^1$ is H;

$R^{1a}$ is selected from: H, $OR^{4a}$, $C_1$-$C_6$ alkyl, $C_4$-$C_{11}$ cycloalkylalkyl, aryl, aryl($C_1$-$C_{10}$ alkyl)-, or heteroaryl($C_1$-$C_{10}$ alkyl)-;

$R^{1b}$ is H;

alternatively, $R^{1a}$ and $R^{1b}$ can be taken together with the nitrogen atom to which they are attached to form a 5-6 membered heterocyclic ring optionally containing 1 additional heteroatom selected from O, N or S, said heterocyclic ring being substituted with 0-2 $R^4$;

$R^2$ is selected from H or $CH_3$;

$R^3$ is selected from hydroxy, $C_1$-$C_{10}$ alkyloxy, aryloxy, aryl-$C_1$-$C_{10}$ alkoxy, $C_3$-$C_{10}$ alkyloxycarbonyloxyalkoxy, $C_8$-$C_{14}$ arylcarbonyloxyalkoxy, $C_5$-$C_{10}$ alkyldioxolenonylmethoxy, aryldioxolenonylmethoxy, $C_5$-$C_{10}$ cycloalkoxycarbonyloxyalkoxy, $C_5$-$C_{10}$ alkyloxyalkylcarbonyloxyalkyloxy, or N-morpholinoethoxy;

$R^4$, when a substituent on carbon, is independently selected from: H, $C_1$-$C_4$ alkyl, or when $R^4$ is attached to a saturated carbon, it may be =O;

$R^4$, when a substituent on nitrogen, is independently selected from:

H, $C_1$-$C_4$ alkyl, $C_1$-$C_{10}$ alkoxycarbonyl, $C_1$-$C_{10}$ alkylcarbonyl, $C_7$-$C_{11}$ arylcarbonyl, or aryl($C_1$-$C_{10}$ alkoxy)carbonyl;

$R^{4a}$ is selected from: H, $C_1$-$C_6$ alkyl, $C_7$-$C_{14}$ arylalkyl.

Further preferred compounds of this invention also include compounds, or pharmaceutically acceptable salt or prodrug or tautomeric forms thereof, wherein:

$R^1$ is selected from H, aryl($C_1$-$C_{10}$ alkoxy)carbonyl, or $C_2$-$C_{10}$ alkoxycarbonyl;

$R^{1a}$ is H;

$R^{1b}$ is H;

$R^2$ is selected from H, or $CH_3$;

$R^3$ is selected from hydroxy, $C_1$-$C_{10}$ alkyloxy, aryloxy, aryl-$C_1$-$C_{10}$ alkoxy, $C_3$-$C_{10}$ alkyloxycarbonyloxyalkoxy, $C_8$-$C_{14}$ arylcarbonyloxyalkoxy, $C_5$-$C_{10}$ alkyldioxolenonylmethoxy, aryldioxolenonylmethoxy, $C_5$-$C_{10}$ cycloalkoxycarbonyloxyalkoxy, $C_5$-$C_{10}$ alkyloxyalkylcarbonyloxyalkyloxy, or N-morpholinoethoxy.

Specifically preferred compounds of this invention are compounds, or pharmaceutically acceptable salt or prodrug or tautomeric forms thereof, selected from the group consisting of:

5(R,S)-3-[3-(4-amidinophenyl)isoxazolin-5-ylacetyl]aminopropanoic acid;

3(R,S)-5(R,S)-3-[3-(4-amidinophenyl)isoxazolin-5-ylacetyl]amino-3-methylpropanoic acid;

methyl 5(R,S)-3-[3-(4-N-n-butylamidinophenyl)isoxazolin-5-ylacetyl]aminopropanoate;

5(R,S)-3-[3-(4-N-n-butylamidinophenyl)isoxazolin-5-ylacetyl]aminopropanoic acid;

methyl 5(R,S)-3-[3-(4-N-propylamidinophenyl)isoxazolin-5-ylacetyl]aminopropanoate;

5(R,S)-3-[3-(4-N-propylamidinophenyl)isoxazolin-5-ylacetyl]aminopropanoic acid;

ethyl 5(R,S)-3-[3-(4-N-ethylamidinophenyl)isoxazolin-5-ylacetyl]aminopropanoate;

5(R,S)-3-[3-(4-N-ethylamidinophenyl)isoxazolin-5-ylacetyl]aminopropanoic acid;

ethyl 5(R,S)-3-[3-(4-N-methylamidinophenyl)isoxazolin-5-ylacetyl]aminopropanoate;

5(R,S)-3-[3-(4-N-methylamidinophenyl)isoxazolin-5-ylacetyl]aminopropanoic acid;

ethyl 5(R,S)-3-[3-(4-N-n-pentylamidinophenyl)isoxazolin-5-ylacetyl]aminopropanoate;
5(R,S)-3-[3-(4-N-n-pentylamidinophenyl)isoxazolin-5-ylacetyl]aminopropanoic acid;
ethyl 5(R,S)-3-[3-(4-N-isopentylamidinophenyl)isoxazolin-5-ylacetyl]aminopropanoate;
5(R,S)-3-[3-(4-N-isopentylamidinophenyl)isoxazolin-5-ylacetyl]aminopropanoic acid;
ethyl 5(R,S)-3-[3-(4-N-isobutylamidinophenyl)isoxazolin-5-ylacetyl]aminopropanoate;
5(R,S)-3-[3-(4-N-isobutylamidinophenyl)isoxazolin-5-ylacetyl]aminopropanoic acid;
ethyl 5(R,S)-3-[3-(4-N-phenethylamidinophenyl)isoxazolin-5-ylacetyl]aminopropanoate;
5(R,S)-3-[3-(4-N-phenethylamidinophenyl)isoxazolin-5-ylacetyl]aminopropanoic acid;
ethyl 5(R,S)-3-[3-(4-N-pyridinylethylamidinophenyl)isoxazolin-5-ylacetyl]aminopropanoate;
5(R,S)-3-[3-(4-N-pyridinylethylamidinophenyl)isoxazolin-5-ylacetyl]aminopropanoic acid;
ethyl 5(R,S)-3-[3-(4-N-cyclohexylmethylamidinophenyl)isoxazolin-5-ylacetyl]aminopropanoate;
5(R,S)-3-[3-(4-N-cyclohexylmethylamidinophenyl)isoxazolin-5-ylacetyl]aminopropanoic acid;
methyl 5(R,S)-3-[3-(4-N-tetrahydrofuranylmethylamidinophenyl)isoxazolin-5-ylacetyl]aminopropanoate;
5(R,S)-3-[3-(4-N-tetrahydrofuranylmethylamidinophenyl)isoxazolin-5-ylacetyl]aminopropanoic acid;
Ethyl 5(R,S)-3-[3-(4-N-phenylamidinophenyl)isoxazolin-5-ylacetyl]aminopropanoate;
5(R,S)-3-[3-(4-N-phenylamidinophenyl)isoxaolin-5-ylacetyl]aminopropanoic acid.

In the present invention it has been discovered that the compounds of Formula I above are useful as inhibitors of glycoprotein IIb/IIIa (GPIIb/IIIa). The compounds of the present invention inhibit the activation and aggregation of platelets induced by all known endogenous platelet agonists.

The present invention also provides pharmaceutical compositions comprising a compound of Formula I and a pharmaceutically acceptable carrier.

The compounds of Formula I of the present invention are useful for the treatment (including prevention) of thromboembolic disorders. The term thromboembolic disorders as used herein includes conditions involving platelet activation and aggregation, such as arterial or venous cardiovascular or cerebrovascular thromboembolic disorders, including, for example, unstable angina, first or recurrent myocardial infarction, ischemic sudden death, transient ischemic attack, stroke, atherosclerosis, venous thrombosis, deep vein thrombosis, thrombophlebitis, arterial embolism, coronary and cerebral arterial thrombosis, myocardial infarction, cerebral embolism, kidney embolisms, pulmonary embolisms, or diabetes, comprising administering to a mammal in need of such treatment a therapeutically effective amount of a compound of Formula I described above.

The compounds of the present invention are useful for inhibiting the binding of fibrinogen to blood platelets, inhibiting aggregation of blood platelets, treating thrombus formation or embolus formation, or preventing thrombus or embolus formation in a mammal. The compounds of the invention may be used as a medicament for blocking fibrinogen from acting at its receptor site in a mammal.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption, and where the aggregated platelets may form thrombi and thromboemboli. The compounds of the present invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between GPIIb/IIIa on the platelet membranes and fibrinogen adsorbed to the surface of the circuit. Platelets released from artificial surfaces show impaired homeostatic function. Compounds of the invention may be administered to prevent adhesion.

Other applications of these compounds include prevention of platelet thrombosis, thromboembolism, and reocclusion during and after thrombolytic therapy and prevention of platelet thrombosis, thromboembolism and reocclusion after angioplasty of coronary and other arteries and after coronary artery bypass procedures. The compounds of the present invention may also be used to prevent myocardial infarction. The compounds of the present invention are useful as thrombolytics for the treatment of thromboembolic disorders.

The compounds of the present invention can also be administered in combination with one or more additional therapeutic agents select from: anti-coagulant or coagulation inhibitory agents, such as heparin or warfarin; anti-platelet or platelet inhibitory agents, such as aspirin, piroxicam, or ticlopidine; thrombin inhibitors such as boropeptides, hirudin or argatroban; or thrombolytic or fibrinolytic agents, such as plasminogen activators, anistreplase, urokinase, or streptokinase.

The compounds of Formula I of the present invention can be administered in combination with one or more of the foregoing additional therapeutic agents, thereby to reduce the doses of each drug required to achieve the desired therapeutic effect. Thus, the combination treatment of the present invention permits the use of lower doses of each component, with reduced adverse, toxic effects of each component. A lower dosage minimizes the potential of side effects of the compounds, thereby providing an increased margin of safety relative to the margin of safety for each component when used as a single agent. Such combination therapies may be employed to achieve synergistic or additive therapeutic effects for the treatment of thromboembolic disorders.

By "therapeutically effective amount" it is meant an amount of a compound of Formula I that when administered alone or in combination with an additional therapeutic agent to a cell or mammal is effective to prevent or ameliorate the thromboembolic disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The term anti-coagulant agents (or coagulation inhibitory agents), as used herein, denotes agents that inhibit blood coagulation. Such agents include warfarin (available as COUMADIN ™) and heparin.

The term anti-platelet agents (or platelet inhibitory agents), as used herein, denotes agents that inhibit platelet function such as by inhibiting the aggregation, adhesion or granular secretion of platelets. Such agents include the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicyclic acid or ASA), and piroxicam. Piroxicam is commercially available from Pfizer Inc. (New York, N.Y.), as FELDANE ™. Other suitable anti-platelet agents include ticlopidine, including pharmaceutically acceptable salts or prodrugs thereof. Ticlopidine is also a preferred compound since it is known to be gentle on the gastro-intestinal tract in use. Still other suitable platelet inhibitory agents include thromboxane-A2-receptor antagonists and thromboxane-A2-synthetase inhibitors, as well as pharmaceutically acceptable salts or prodrugs thereof.

The phrase thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. Such inhibitors include boropeptides, hirudin and argatroban, including pharmaceutically acceptable salts and prodrugs thereof. Preferably the thrombin inhibitors are boropeptides. By boropeptides, it is meant, N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin. Boropeptide thrombin inhibitors include compounds described in Kettner et al., U.S. Pat. No. 5,187,157 and European Patent Application Publication Number 293 881A2, the disclosures of which are hereby incorporated herein by reference. Other suitable boropeptide thrombin inhibitors include those disclosed in PCT Application Publication Number 92/07869 and European Patent Application Publication Number 471 651 A2, the disclosures of which are hereby incorporated herein by reference, in their entirety.

The phrase thrombolytics (or fibrinolytic) agents (or thrombolytics or fibrinolytics), as used herein, denotes agents that lyse blood clots (thrombi). Such agents include tissue plasminogen activator, anistreplase, urokinase or streptokinase, including pharmaceutically acceptable salts or prodrugs thereof. Tissue plasminogen activator (tPA) is commercially available from Genentech Inc., South San Francisco, Calif. The term anistreplase, as used herein, refers to anisoylated plasminogen streptokinase activator complex, as described, for example, in European Patent Application No. 028,489, the disclosures of which are hereby incorporated herein by reference herein, in their entirety. Anistreplase is commercially available as EMINASE ™. The term urokinase, as used herein, is intended to denote both dual and single chain urokinase, the latter also being referred to herein as prourokinase.

Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

GPIIb/IIIa is known to be overexpressed in metastatic tumor cells. The compounds or combination products of the present invention may also be useful for the treatment, including prevention, of metastatic cancer.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable occurs more than one time in any constituent or in any formula, its definition on each occurrence is independent of its definition at every other occurrence.

Combinations of substituents and/or variables are permissible only if such combinations result in stable compounds. By stable compound or stable structure it is meant herein a compound that is sufficiently robust to survive isolation to a useful degree of purity from a reaction mixture, and formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1$-$C_{10}$" denotes alkyl having 1 to 10 carbon atoms); "haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)); "alkoxy" represents an alkyl group of indicated number of carbon atoms attached through an oxygen bridge; "cycloalkyl" is intended to include saturated ring groups, including mono-, bi- or poly-cyclic ring systems, such as cyclopropyl, cyclobutyl, cyclopentyl, cyclohexyl, cycloheptyl, cyclooctyl, and adamantyl; and "biycloalkyl" is intended to include saturated bicyclic ring groups such as [3.3.0]bicyclooctane, [4.3.0]bicyclononane, [4.4.0]bicyclodecane (decalin),

[2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyl" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, "heterocycle" or "heteroaryl" is intended to include stable 5- to 7-membered monocyclic or bicyclic rings and stable 7- to 10-membered bicyclic rings where the heterocycle or heteroaryl may be either saturated or unsaturated, and where the heterocycle or heteroaryl comprises from 1 to 4 heteroatoms independently selected from the group consisting of N, O and S, wherein the nitrogen and sulfur heteroatoms may optionally be oxidized, and the nitrogen heteroatom may optionally be quaternized, including a bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on a carbon or nitrogen atom if the resulting compound is stable. Examples of such heterocycles or heteroaryls include, but are not limited to, azocinyl, furanyl, imidazolidinyl, imidazolinyl, imidazolyl, oxazolyl, oxazolinyl, thiazolyl, isothiazolyl, isoxazolyl, isoxazolinyl, isothiazolinyl, thiazolinyl, morpholinyl, thiomorpholinyl, piperazinyl, piperidinyl, 4-piperidonyl, pyranyl, pyrazinyl, pyrazolidinyl, pyrazolinyl, pyrazolyl, pyridazinyl, pyridinyl, pyrimidinyl, pyrrolidinyl, pyrrolinyl, 2-pyrrolidonyl, pyrrolinyl, pyrrolyl, 2H-pyrrolyl, tetrahydrofuranyl, tetrazolyl, thienyl, triazolyl, and triazinyl.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like. Examples of representative carboxyl and amino prodrugs are included under the definition of $R^1$ and $R^3$.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

The disclosures of all of the references cited herein are hereby incorporated herein by reference in their entirety.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The following abbreviations are used herein:

| | |
|---|---|
| β-Ala | 3-aminopropionic acid |
| DCC | 1,3-dicyclohexylcarbodiimide |
| DEC | 1-(3-dimethylaminopropyl)-3-ethylcarbdi-imide hydrochloride |
| DCM | dichloromethane |
| DMAP | 4-dimethylaminopyridine |
| DMF | N,N-dimethylformamide |
| EtOAc | ethyl acetate |
| EtOH | ethyl alcohol |
| NaOTMS | sodium trimethylsilanolate |
| NCS | N-chlorosuccinimide |
| pyr | pyridine |
| TBTU | 2-(1H-Benzotriazol-1-yl)-1,1,3,3-tetramethyluronium tetrafluoroborate |
| TFA | trifluoroacetic acid |
| THF | tetrahydrofuran |

Synthesis of the compounds of this invention relies on the dipolar cycloaddition of nitrile oxides with an appropriate dipolarophile as the key step (for reviews of 1,3-dipolar cycloaddition chemistry, see 1,3-Dipolar Cycloaddition Chemistry (Padwa, ed.), Wiley, New York, 1984; Kanemasa and Tsuge, *Heterocycles* 1990, 30, 719). Scheme I describes one synthetic sequence to the compounds of this invention. An appropriately substituted hydroxylamine is treated with NCS in DMF according to the method of Liu, et. al. (*J. Org. Chem.* 1980, 45, 3916). The resulting hydroximinoyl chloride is then dehydrohalogenated in situ using TEA to give a nitrile oxide, which undergoes a 1,3-dipolar cycloaddition to a suitably substituted alkene to afford the isoxazoline. Alternatively, the oxime may be oxidatively chlorinated, dehydrochlorinated and the resulting nitrile oxide trapped by a suitable alkene under phase transfer conditions according to the method of Lee (*Synthesis* 1982, 508). Intermediates containing alkali-sensitive functionality, such as nitrile, may be deesterified with excellent chemoselectivity using sodium trimethylsilanolate according to the procedure of Laganis and Ehenard (*Tetrahedron Lett.* 1984, 25, 5831). Coupling to an appropriately substituted α- or β-amino ester using standard coupling reagents, such as DCC/HOBt, affords a nitrile-amide. The nitrile is then converted to the amidine via the imidate or thioimidate under standard conditions followed by ester saponification (LiOH, THF/H$_2$O).

Scheme I

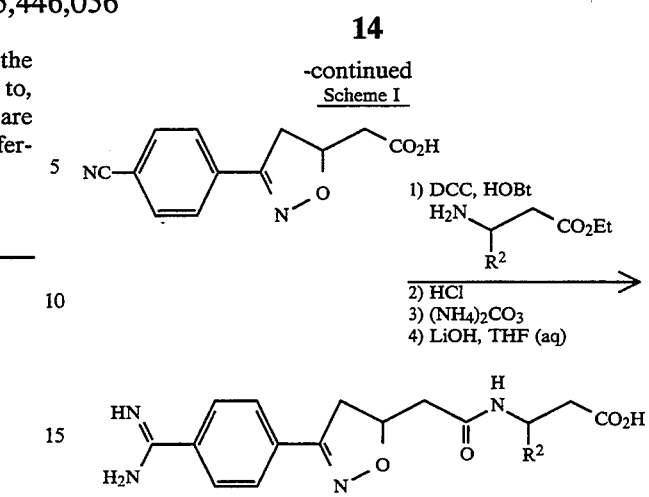

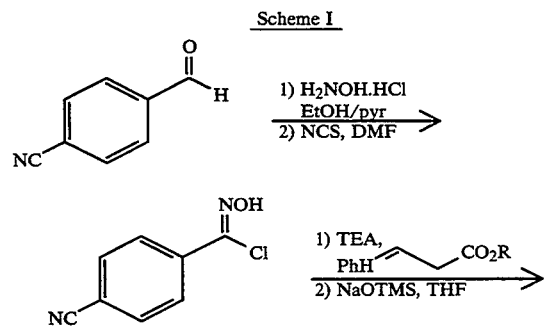

The appropriately substituted racemic β-alkyl-β-amino acids may be purchased commercially or, as is shown in Scheme II, Method 1, prepared through the reaction of dialkylcuprates or alkyllithiums with 4-benzoyloxy-2-azetidinone followed by treatment with anhydrous ethanol. Enantiomerically pure β-amino acids can be obtained through optical resolution of the racemic mixture or can be prepared using numerous methods, including: Arndt-Eistert homologation of the corresponding α-amino acids as shown in Scheme II, Method 2 (see Meier, and Zeller, *Angew, Chem. Int. Ed. Engl.* 1975, 14, 32; Rodriguez, et. al. *Tetrahedron Lett.* 1990, 31, 5153; Greenlee, *J. Med. Chem.* 1985, 28, 434 and references cited within); and through an enantioselective hydrogenation of a dehydroamino acid as is shown in Scheme II, Method 3 (see Asymmetric Synthesis, Vol. 5, (Morrison, ed.) Academic Press, New York, 1985). A comprehensive treatise on the preparation of β-amino acid derivatives may be found in patent application WO 9307867, the disclosure of which is hereby incorporated by reference.

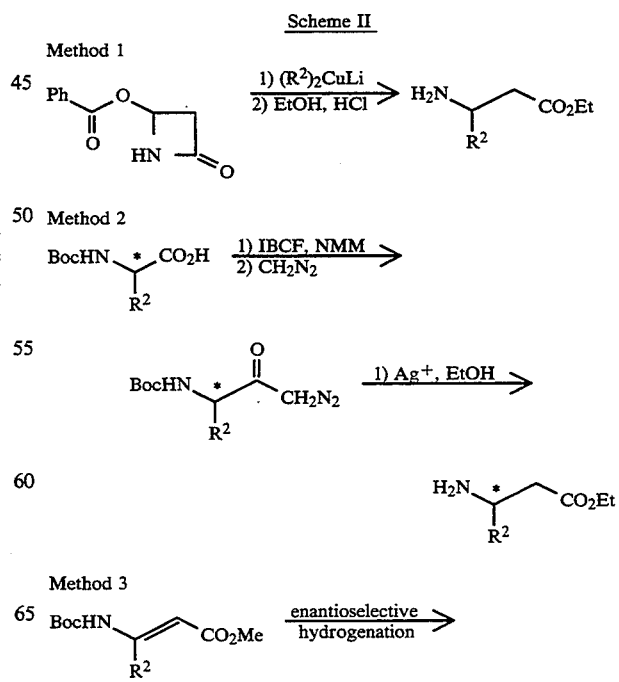

Scheme II (continued)

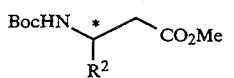

Scheme III

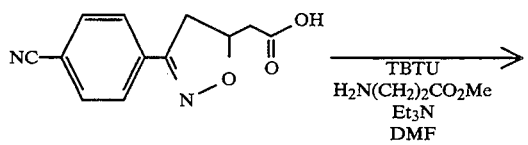

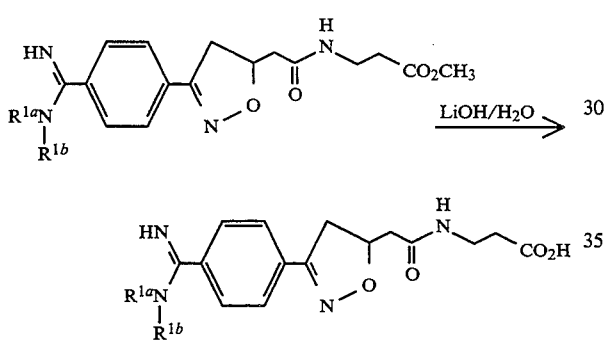

Alternatively, as illustrated in Scheme IV, the intermediate [3-(4-cyanophenyl)isoxazolin-5-yl]acetic acid may be first converted to the corresponding amidine by conversion to the imidate or thioimidate followed by addition of an appropriately substituted amine. The resulting amidinoester is then protected, and the ester saponified. The acid which is generated may be coupled directly to an appropriately substituted β-amino acid under standard peptide coupling conditions as described above. Saponification followed by deprotection of the amidine yields the desired compounds.

Scheme IV

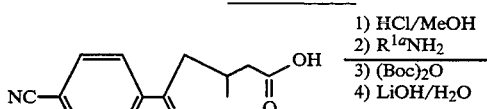

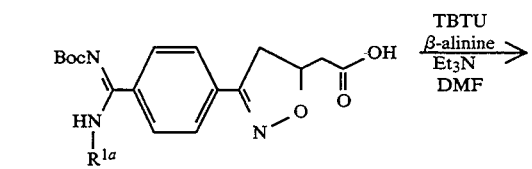

Scheme IV (continued)

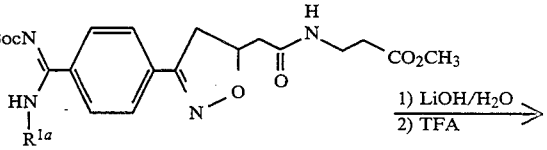

Compounds of the invention wherein $R^1$ and $R^{1a}$ combined to form a cyclic amidine can be prepared by the addition of an appropriate diamine to the imidate intermediates in Schemes I, III and IV above. The addition is carried out under thermolytic conditions as described by Slavica, et. al. (*J. Med. Chem*, 1994, 37, 1874). An example of such a transformation is illustrated in Scheme V below.

Scheme V

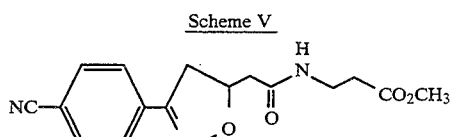

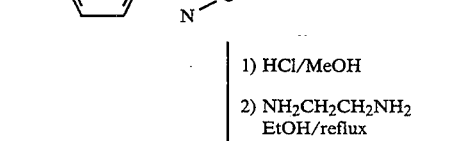

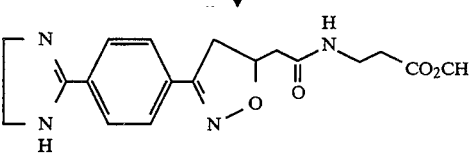

The compounds of this invention and their preparation can be further understood by the following procedures and examples, which exemplify but do not constitute a limit of their invention.

EXAMPLE 1

5(R,S)-3-[3-(4-Amidinophenyl)isoxazolin-5-ylacetyl]aminopropanoic Acid

Part A. 4-Cyanobenzaldoxime

This material was prepared from 4-cyanobenzaldehyde according to Kawase and Kikugawa (*J. Chem. Soc., Perkin Trans I* 1979, 643).

Part B. 4-Cyanobenzoximinoyl Chloride

To a solution of 4-cyanobenzoxime (7.64 g, 52.3 mmol) in DMF (50 mL) was added NCS (6.98 g, 52.3 mmol) in three portions. The resulting mixture was stirred for 20 hours. The mixture was diluted with EtOAc and washed with water (4×), 0.1M HCl, sat. NaHCO$_3$ and sat. NaCl and dried over anhydrous MgSO$_4$. The resulting filtrate was concentrated in vacuo and the residue crystallized from EtOAc/hexanes, giving 5.80 g (61%); Anal Calc for C$_8$H$_5$ClN$_2$O: C, 53.21; H, 2.79; N, 15.51; Cl, 19.63; Found: C, 53.49; H, 2.91; N, 15.41; Cl, 19.52.

Part C. Methyl 3-Butenoate

To a solution of vinylacetic acid (9.87 mL, 0.116 mol), methanol (4.70 mL, 0.116 mol) and DMAP (100 mg, 1.64 mmol) in DCM (100 mL) at room temperature was added DCC (26.36 g, 0.128 mmol). The resulting mixture was stirred for 18 hours. The mixture was filtered and the filtrate then washed with sat. NaHCO$_3$ and dried over anhydrous MgSO$_4$ and distilled at atmospheric pressure (bp: 100°–105° C.), giving 8.32 g (72%).

Part D. Methyl 5(R,S)-[3-(4-Cyanophenyl)isoxazolin-5-yl]acetate

To a solution of 4-cyanobenzoximinoyl chloride (3.36 g, 18.6 mmol) and methyl 3-butenoate (3.72 g, 37.2 mmol) in benzene (30 mL) was added TEA (2.60 mL, 19 mmol). The resulting mixture was heated at reflux for 2 hours, cooled to room temperature and diluted with EtOAc. The mixture was washed with 0.1M HCl, water and sat. NaCl and dried over anhydrous MgSO$_4$. The resulting filtrate was concentrated in vacuo and the residue crystallized from EtOAc/hexanes, giving 3.68 g (81%); mp: 120.1°–120.5° C.; $^1$H NMR (300 MHz, CDCl$_3$) 67 7.72 (AB quartet, Δ=22.7 Hz, J=8.4 Hz, 4H), 5.16 (m, 1H), 3.72 (s, 3H), 3.54 (dd, J=16.8, 10.6 Hz, 1H), 3.13 (dd, J=16.8, 7.7 Hz, 1H), 2.90 (dd, J=16.1, 5.7 Hz, 1H), 2.67 (dd, J=16.1, 7.7 Hz, 1H); Anal Calc for C$_{13}$H$_{12}$N$_2$O$_3$: C, 63.93; H, 4.95; N, 11.47; Found: C, 63.63; H, 4.81; N, 11.52.

Part E. 5(R,S)-[3-(4-Cyanophenyl)isoxazolin-5-yl]acetic Acid

To a solution of methyl 5(R,S)-[3-(4-cyanophenyl)isoxazolin-5-yl]acetate (108 mg, 0.442 mmol) in THF (3 mL) was added 1M NaOTMS in THF (1 mL, 1 mmol). The resulting mixture was stirred overnight at room temperature, then diluted with EtOAc and 5% citric acid. The aqueous portion was washed with EtOAc, the combined organic portion washed with water then extracted with 5% NaHCO$_3$. The alkaline solution was washed with EtOAc and acidified with solid citric acid. The now acidic solution was extracted with EtOAc, and the combined organic washed with sat. NaCl and dried over anhydrous MgSO$_4$. Concentration of the resulting filtrate in vacuo followed by pumping to constant weight afforded 80 mg (79%) of the desired acid; mp: 179.2°–181.5° C.

Part F. Ethyl 5(R,S)-3-[3-(4-Cyanophenyl)isoxazolin-5-ylacetyl]aminopropanoate To a suspension of 5(R,S)-[3-(4-cyanophenyl)isoxazolin-5-yl]acetic acid (77 mg, 0.334 mmol), ethyl 3-aminopropionate (47 mg, 0.337 mmol) and TBTU (108 mg, 0.336 mmol) in EtOAc (5 mL) was added TEA (0.2 mL, 1.4 mmol). The resulting mixture was stirred for 2 hours, diluted with EtOAc and washed with 5% citric acid, water, sat. NaHCO$_3$ and sat. NaCl and dried over anhydrous MgSO$_4$. Concentration of the resulting filtrate in vacuo followed by pumping to constant weight afforded 80 mg (76%) of the desired amide; mp: 102.0°–102.9° C.; Anal Calc for C$_{17}$H$_{19}$N$_3$O$_4$: C, 61.99; H, 5.86; N, 12.76; Found: C, 62.04; H, 5.79; N, 12.63.

Part G. Ethyl 5(R,S)-3-[3-(4-Amidinophenyl)isoxazolin-5-ylacetyl]aminopropanoate (Example 3)

Into a solution of ethyl 5(R,S)-3-[3-(4-cyanophenyl)isoxazolin-5-ylacetyl]aminopropanoate (1.65 mg, 5.00 mmol) in 10% DCM/EtOH (165 mL) was bubbled HCl gas for 2 hours. After 18 hours, the solvent was evaporated in vacuo, the residue dissolved in EtOH (100 mL) and ammonium carbonate (14.41 g, 150 mmol) added. The resulting suspension was stirred at room temperature for 18 hours, then filtered and the resulting filtrate concentrated in vacuo. The residue was then crystallized from EtOH/ether, giving 713 mg (41%) of the desired amidine; $^1$H NMR (300 MHz, CD$_3$OD) δ7.88 (AB quartet, Δ=16.8 Hz, J=8.4 Hz, 4H), 5.13 (m, 1H), 4.12 (q, J=7.3 Hz, 2H), 3.58 (dd, J=17.2, 10.6 Hz, 1H), 3.44 (m, 2H), 3.26 (dd, J=17.2, 7.3 Hz, 1H, coincident with solvent), 2.57 (m, 4H), 1.25 (t, J=7.3 Hz, 2H).

Part H. 5(R,S)-3-[3-(4-Amidinophenyl)isoxazolin-5-ylacetyl]aminopropanoic Acid To a solution of ethyl 5(R,S)-3-[3-(4-amidinophenyl)isoxazolin-5-ylacetyl]aminopropanoate (346 mg, 1.00 mmol) in EtOH (6 mL) was added 0.5M LiOH. Upon mixing, a precipitate of the zwitterionic product began to form. After stirring for 18 hours at room temperature, the solid was collected by filtration, affording 365 mg of the title compound; $^1$H NMR (300 MHz, CD$_3$OD) δ7.86 (AB quartet, Δ=18.3 Hz, J=8.4 Hz, 4H), 5.21 (m, 1H), 3.57 (dd, J=17.2, 10.6 Hz, 1H), 3.43 (m, 2H), 3.25 (dd, J=17.2, 7.3 Hz, 1H, coincident with solvent), 2.64 (dd, J=14.6, 6.8 Hz, 1H), 2.52 (m, 3H).

EXAMPLE 23

Ethyl 5(R,S)-3-[3-(4-N-n-Butylamidinophenyl)isoxazolin-5-ylacetyl]aminopropanoate Ethyl 5(R,S)-3-[3-(4-cyanophenyl)isoxazolin-5-ylacetyl]aminopropanoate (0.29 g, 0.92 mmol) was weighed into a 50 ml round bottomed flask, diluted with ethanol (20 ml), cooled in an ice bath, and HCl gas bubbled through the solution for two hours. After 18 hours, the solvent was evaporated in vacuo, the residue was diluted with ethanol (30 ml) and n-butyl amine (0.30 ml, 2.76 mmol) added. The resulting suspension was stirred at room temperature for 18 hours, then filtered and the resulting filtrate concentrated in vacuo. The residue was purified on a plug of silica gel using 10% MeOH/CH$_2$Cl$_2$ as the eluting solvent, to give the title compound (31%). IR (KBr pellet) cm$^{-1}$: 2960, 1734, 1676, 1648, 1590, 1558, 1514, 1466, 1378, 1186. HRMS calc'd for C$_{21}$H$_{30}$N$_4$O$_4$ 403.234531 Found 403.234347.

Using the above-described techniques or variations thereon appreciated by those of skill in the art of chemical synthesis, the compounds of the present invention, including but not limited to, the representative compounds of the present invention set forth in Table 1 and 1A (below) can also be prepared.

Table 1 below sets forth representative compounds of the present invention.

TABLE 1

| Example Number | R$^1$ | R$^2$ | R$^3$ |
|---|---|---|---|
| 1 | H | H | OH |
| 2 | H | H | OMe |
| 3 | H | H | OEt |
| 4 | H | H | (cyclohexyl carbonate group) |

TABLE 1-continued

Structure (I): 4-amidino-phenyl with N-OH (hydroxyimino-aminomethyl) group, connected via CH2-CH(CH2...)-C(=O)-NH-CH(R2)-C(=O)-R3

| Example Number | $R^1$ | $R^2$ | $R^3$ |
|---|---|---|---|
| 5 | H | H | -O-CH2-O-C(=O)-Me |
| 6 | H | H | -O-CH2-O-C(=O)-O-CH2-C(Me)=C(Me)(Me) (pivaloyloxymethyl-type with gem-dimethyl vinyl) |
| 7 | H | H | -O-CH2-C(=O)-OEt |
| 8 | H | H | -O-CH2CH2-N(Et)2 |
| 9 | H | Me | OH |
| 10 | H | Me | OMe |
| 11 | H | Me | OEt |
| 12 | H | Me | -O-CH2-O-C(=O)-O-cyclohexyl |
| 13 | H | Me | -O-CH2-O-C(=O)-Me |
| 14 | H | Me | -O-CH2-C(Me)=C(Me)(Me) ester-type |
| 15 | H | Me | -O-CH2-C(=O)-OEt |
| 16 | H | Me | -O-CH2CH2-N(Et)2 |

TABLE 1A

Structure: $R^{1a}(R^{1b})N-C(=NR^1)$-phenyl connected via CH2-CH2-C(=O)-NH-CH2-CH2-C(=O)-R3, with N-O on central chain.

| Ex. No. | $R^1$ | $R^{1a}$ | $R^{1b}$ | $R^3$ | Mass Spec $(M + H)^+$ |
|---|---|---|---|---|---|
| 20 | H | methyl | H | CO2Me | |
| 21 | H | methyl | H | CO2H | |
| 22 | H | ethyl | H | CO2Me | 361 |
| 23 | H | ethyl | H | CO2H | |
| 24 | H | n-propyl | H | CO2Me | 375 |
| 25 | H | n-propyl | H | CO2H | |
| 26 | H | n-butyl | H | CO2Et | 403 |
| 27 | H | n-butyl | H | CO2H | |
| 28 | H | n-pentyl | H | CO2Na | 389 |
| 29 | H | n-pentyl | H | CO2Et | 417 |
| 30 | H | 3-methyl-1-butyl | H | CO2Na | 389 |
| 31 | H | 3-methyl-1-butyl | H | CO2Et | 417 |
| 32 | H | benzyl | H | CO2Me | 423 |
| 33 | H | benzyl | H | CO2H | |
| 34 | H | phenethyl | H | CO2Na | 423 |
| 35 | H | phenethyl | H | CO2Et | 451 |
| 36 | H | cyclohexylmethyl | H | CO2Me | |
| 37 | H | cyclohexylmethyl | H | CO2H | |
| 38 | H | 1-cyclohexylethyl | H | CO2Me | |
| 39 | H | 1-cyclohexylethyl | H | CO2H | |
| 40 | H | 4-piperidinyl-methyl | H | CO2Me | |
| 41 | H | 4-piperidinyl-methyl | H | CO2H | |
| 42 | H | phenyl | H | CO2Me | |
| 43 | H | phenyl | H | CO2H | |
| 44 | H | OH | H | CO2Me | |
| 45 | H | OH | H | CO2H | |
| 46 | H | $R^{1a}$ and $R^{1b}$ = —(CH2)5— | | CO2Me | |
| 47 | H | $R^{1a}$ and $R^{1b}$ = —(CH2)5— | | CO2H | |
| 48 | $R^1$ and $R^{1a}$ = —(CH2)2— | | H | CO2Me | |
| 49 | $R^1$ and $R^{1a}$ = —(CH2)2— | | H | CO2H | |
| 50 | H | tetrahydrofuranylmethyl | H | CO2Me | |
| 51 | H | tetrahydrofuranylmethyl | | CO2H | |
| 52 | H | cyclopropylmethyl | H | CO2Me | |
| 53 | H | cyclopropylmethyl | H | CO2H | |

Utility

The compounds of this invention possess antiplatelet efficacy, as evidenced by their activity in standard platelet aggregation assays or platelet fibrinogen binding assays, as described below. A compound is considered to be active in these assays if it has an IC50 value of less than about 1 mM. Platelet aggregation and fibrinogen binding assays which may be used to demonstrate the antiplatelet activity of the compounds of the invention are described below.

Platelet Aggregation Assay: Venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 μL of PRP was added to each micro test tube, and transmittance was set to 0%. 20 μL of various agonists (ADP, collagen, arachidonate, epinephrine, thrombin) were added to each tube, and the aggregation profiles were plotted (% transmittance versus time). The results are expressed as % inhibition of agonist-induced platelet aggregation. For the $IC_{50}$ evaluation, the test compounds were added at various concentrations prior to the activation of the platelets. Ester prodrugs were preincubated ($10^{-3}$M F.C.) with 100 IU/ml Porcine liver esterase (Sigma Chemical Co., St. Louis, Mo., #E-3128) for 2 hours at 37° C. Aliquots are then diluted in 0.1M Tris, pH 7.4, to the desired concentrations. Aliquots of 20 μl of the esterase pretreated prodrugs are added to 200 μl of human platelet rich plasma. Samples were placed in platelet profiler (aggregometer) for 8 minutes at 37° C., followed by the addition of 100 μM Adenosine Diphosphate, (Sigma Chemical Co., St. Louis, Mo., #A-6521), to induce platelet aggregation. Platelet aggregation was allowed to proceed for 5 minutes. Percent inhibition is calculated using percent aggregation in the presence of the test compound divided by percent aggregation of control, times 100. This value is subtracted from 100, yielding percent inhibition. Calculation of IC50 is performed on a Texas Instruments TI59 with an IC50 program.

Platelet Aggregation Assay; Venous blood was obtained from the arm of a healthy human donor who was drug-free and aspirin-free for at least two weeks prior to blood collection. Blood was collected into 10 mL citrated Vacutainer tubes. The blood was centrifuged for 15 minutes at 150×g at room temperature, and platelet-rich plasma (PRP) was removed. The remaining blood was centrifuged for 15 minutes at 1500×g at room temperature, and platelet-poor plasma (PPP) was removed. Samples were assayed on a aggregometer (PAP-4 Platelet Aggregation Profiler), using PPP as the blank (100% transmittance). 200 μL of PRP was added to each micro test tube, and transmittance was set to 0%. 20 μL of various agonists (ADP, collagen, arachidonate, epinephrine, thrombin) were added to each tube, and the aggregation profiles were plotted (% transmittance versus time). The results are expressed as % inhibition of agonist-induced platelet aggregation. For the $IC_{50}$ evaluation, the test compounds were added at various concentrations prior to the activation of the platelets.

Purified GPIIb/IIIa-Fibrinogen Binding ELISA

The following reagents are used in the GPIIb/IIIa-fibrinogen binding ELISA:
   purified GPIIb/IIIa (148.8 ug/mL); biotinylated fibrinogen (~1 mg/mL or 3000 nM); anti-biotin alkaline phosphatase conjugate (Sigma no. A7418);
   flat-bottom, high binding, 96-well plates (Costar Cat. no. 3590);
   phosphatase substrate (Sigma 104) (40 mg capsules);
   bovine serum albumin (BSA) (Sigma no. A3294);
   Alkaline Phosphatase buffer —0.1M glycine-HCl, 1 mM $MgCl_2.6H_2O$, 1 mM $ZnCl_2$, pH 10.4;
   Binding buffer —20 mM Tris-HCl, 150 mM NaCl, 1 mM $CaCl_2.2H_2O$, 0.02% $NaN_3$, pH 7.0;
   Buffer A —50 mM Tris-HCl, 100 mM NaCl, 2 mM $CaCl_2.2H_2O$, 0.02% $NaN_3$, pH 7.4;
   Buffer A+3.5% BSA (Blocking buffer);
   Buffer A+0.1% BSA (Dilution buffer); 2N NaOH.

The following method steps are used in the GPIIb/IIIa-fibrinogen binding ELISA:
   Coat plates with GPIIb/IIIa in Binding buffer (125 ng/100 uL/well) overnight at 4° C. (Leave first column uncoated for non-specific binding). Cover and freeze plates at —70° C. until used. Thaw plate 1 hour at room temperature or overnight at 4° C. Discard coating solution and wash once with 200 uL Binding buffer per well. Block plate 2 hours at room temperature on shaker with 200 ul Buffer A+3.5% BSA (Blocking buffer) per well. Discard Blocking buffer and wash once with 200 uL Buffer A+0.1% BSA (Dilution buffer) per well. Pipet 11 uL of test compound (10× the concentration to be tested in Dilution buffer) into duplicate wells. Pipet 11 ul Dilution buffer into non-specific and total binding wells. Add 100 uL Biotinylated fibrinogen (1/133 in Dilution buffer, final concentration=20 nM) to each well. Incubate plates for 3 hours at room temperature on a plate shaker. Discard assay solution and wash twice with 300 uL Binding buffer per well. Add 100 uL Anti-biotin alkaline phosphatase conjugate (1/1500 in Dilution buffer) to each well. Incubate plates for 1 hour at room temperature on plate shaker. Discard conjugate and wash twice with 300 51 Binding buffer per well. Add 100 uL Phosphatase substrate (1.5 mg/ml in Alkaline phosphatase buffer) to each well. Incubate plate at room temperature on shaker until color develops. Stop color development by adding 25 uL 2N NaOH per well. Read plate at 405 nm. Blank against non-specific binding (NSB) well. % Inhibition is calculated as 100 —(Test Compound Abs/Total Abs)×100.

Platelet-Fibrinogen Binding Assay: Binding of $^{125}$I-fibrinogen to platelets was performed as described by Bennett et al. (1983) Proc. Natl. Acad. Sci. USA 80: 2417–2422, with some modifications as described below. Human PRP (h-PRP) was applied to a Sepharose column for the purification of platelet fractions. Aliquots of platelets ($5 \times 10^8$ cells) along with 1 mM calcium chloride were added to removable 96 well plates prior to the activation of the human gel purified platelets (h-GPP). Activation of the human gel purified platelets was achieved using ADP, collagen, arachidonate, epinephrine, and/or thrombin in the presence of the ligand, $^{125}$I-fibrinogen. The $^{125}$I-fibrinogen bound to the activated platelets was separated from the free form by centrifugation and then counted on a gamma counter. For an $IC_{50}$ evaluation, the test compounds were added at various concentrations prior to the activation of the platelets.

The compounds of Formula I of the present invention may also possess thrombolytic efficacy, that is, they are capable of lysing (breaking up) already formed platelet-rich fibrin blood clots, and thus are useful in treating a thrombus formation, as evidenced by their activity in the tests described below. Preferred compounds of the present invention for use in thrombolysis include those compounds having an $IC_{50}$ value (that is, the molar concentration of the compound capable of achieving 50% clot lysis) of less than about 1 mM, more preferably an $IC_{50}$ value of less than about 0.1 mM.

Thrombolytic Assay: Venous blood was obtained from the arm of a healthy human donor who was drug-free and aspirin free for at least two weeks prior to blood collection, and placed into 10 ml citrated Vacutainer tubes. The blood was centrifuged for 15 minutes at 1500×g at room temperature, and platelet rich plasma (PRP) was removed. To the PRP was then added $1 \times 10^{-3}$M of the agonist ADP, epinephrine, collagen, arachidonate, serotonin or thrombin, or a mixture thereof, and the PRP incubated for 30 minutes. The PRP was centrifuged for 12 minutes at 2500×g at room temperature. The supernatant was then poured off, and the platelets remaining in the test tube were resuspended in platelet poor plasma (PPP), which served as a plasminogen source. The suspension was then assayed on a Coulter Counter (Coulter Electronics, Inc., Hialeah, Fa.), to determine the platelet count at the zero time point. After obtaining the zero time point, test compounds were added at various concentrations. Test samples were taken at various time points and the platelets were counted using the Coulter Counter. To determine the percent of lysis, the platelet count at a time point subsequent to the addition of the test compound was subtracted from the platelet count at the zero time point, and the resulting number divided by the platelet count at the zero time point. Multiplying this result by 100 yielded the percentage of clot lysis achieved by the test compound. For the $IC_{50}$ evaluation, the test compounds were added at various concentrations, and the percentage of lysis caused by the test compounds was calculated.

The compounds of Formula I of the present invention are also useful for administration in combination with anti-coagulant agents such as warfarin or heparin, or antiplatelet agents such as aspirin, piroxicam or ticlopidine, or thrombin inhibitors such as boropeptides, hirudin or argatroban, or thrombolytic agents such as tissue plasminogen activator, anistreplase, urokinase or streptokinase, or combinations thereof.

Table 2 below sets forth the biological activity of representative compounds of the present invention. The indicated compounds were tested for their ability to inhibit platelet aggregation (using platelet rich plasma (PRP)). The $IC_{50}$ value (the concentration of antagonist which inhibits platelet aggregation by 50% relative to a control lacking the antagonist) is shown. In Table 5 the $IC_{50}$ values are expressed as: $+++ = IC_{50}$ of $<10$ μM; $++ = IC_{50}$ of 10–50 μM; $+ = IC_{50}$ of 50–100 μM (μM = micromolar).

TABLE 2

| Ex. No. | PRP $IC_{50}$ |
|---|---|
| 1 | +++ |
| 21 | +++ |
| 23 | +++ |
| 25 | +++ |
| 26 | +++ |
| 27 | +++ |
| 28 | +++ |
| 29 | +++ |
| 31 | +++ |
| 32 | +++ |

Dosage and Formulation

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an anti-aggregation agent.

The compounds of this invention can be administered by any means that produces contact of the active agent with the agent's site of action, glycoprotein IIb/IIIa (GPIIb/IIIa), in the body of a mammal. They can be administered by any conventional means available for use in conjunction with pharmaceuticals, either as individual therapeutic agents or in a combination of therapeutic agents, such as a second antiplatelet agent such as aspirin or ticlopidine which are agonist-specific. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

A large number of tablets are prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension:

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent selected from: an anti-coagulant agent such as warfarin or heparin; an anti-platelet agent such as aspirin, piroxicam or ticlopidine; a thrombin inhibitor such as a boropeptide thrombin inhibitor, or hirudin; or a thrombolytic agent such as plasminogen activators, such as tissue plasminogen activator, anistreplase, urokinase or streptokinase. The compound of Formula I and such second therapeutic agent can be administered separately or as a physical combination in a single dosage unit, in any dosage form and by various routes of administration, as described above.

The compound of Formula I may be formulated together with the second therapeutic agent in a single dosage unit (that is, combined together in one capsule, tablet, powder, or liquid, etc.). When the compound of Formula I and the second therapeutic agent are not formulated together in a single dosage unit, the compound of Formula I and the second therapeutic agent (anti-coagulant agent, anti-platelet agent, thrombin inhibitor, and/or thrombolytic agent) may be administered essentially at the same time, or in any order; for example the compound of Formula I may be administered first, followed by administration of the second agent (anti-coagulant agent, anti-platelet agent, thrombin inhibitor, and/or thrombolytic agent). When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent (anti-coagulant agent, anti-platelet agent, thrombin inhibitor, and/or thrombolytic agent) are both administered by the same route (that is, for example, both orally), if desired, they may each be administered by different routes and in different dosage forms (that is, for example, one component of the combination product may be administered orally, and another component may be administered intravenously).

The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above.

Although the proper dosage of the compound of Formula I when administered in combination with the second therapeutic agent will be readily ascertainable by a medical practitioner skilled in the art, once armed with the present disclosure, by way of general guidance, where the compounds of this invention are combined with anti-coagulant agents, for example, a daily dosage may be about 0.1 to 100 milligrams of the compound of Formula I and about 1 to 7.5 milligrams of the anti-coagulant, per kilogram of patient body weight. For a tablet dosage form, the novel compounds of this invention generally may be present in an amount of about 5 to 10 milligrams per dosage unit, and the anti-coagulant in an amount of about 1 to 5 milligrams per dosage unit.

Where the compounds of Formula I are administered in combination with a second anti-platelet agent, by way of general guidance, typically a daily dosage may be about 0.01 to 25 milligrams of the compound of Formula I and about 50 to 150 milligrams of the additional anti-platelet agent, preferably about 0.1 to 1 milligrams of the compound of Formula I and about 1 to 3 milligrams of antiplatelet agents, per kilogram of patient body weight.

Further, by way of general guidance, where the compounds of Formula I are adminstered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is,
reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the inhibition of platelet aggregation, the treatment of blood clots, and/or the treatment of thromboembolic disorders, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

What is claimed is:

1. A compound of Formula I:

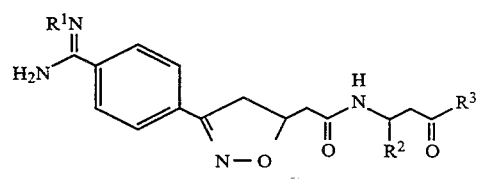

or a pharmaceutically acceptable salt form thereof wherein:

$R^1$ and $R^{1a}$ are independently selected from: H $C_1$–$C_{10}$ alkyl, $C_2$–$C_6$ alkenyl, $C_3$–$C_{11}$ cycloalkyl, $C_4$–$C_{11}$ cycloalkyalkyl, aryl, aryl-$C_1$–$C_{10}$ alkyl, $C_2$–$C_7$ alkylcarbonyl, arylcarbonyl, $C_2$–$C_{10}$ alkoxycarbonyl, $C_4$–$C_{11}$ cycloalkoxycarbonyl, $C_7$–$C_{14}$ bicycloalkoxycarbonyl, aryloxycarbonyl, or aryl(-$C_1$–$C_{10}$ alkoxy)carbonyl;

$R^2$ is selected from H or $CH_3$;

$R^3$ is selected from hydroxy, $C_1$ to $C_{10}$ alkyloxy, $C_3$ to $C_{11}$ cycloalkyloxy, $C_6$ to $C_{10}$ aryloxy, aryl-$C_1$ to $C_{10}$ alkyloxy, $C_3$ to $C_{10}$ alkylcarbonyloxyalkyloxy, $C_3$ to $C_{10}$ alkoxycarbonyloxalkyloxy, $C_2$ to $C_{10}$ alkoxycarbonyloxy, $C_5$ to $C_{10}$ cycloalkylcarbonylocyalkyloxy, $C_5$ to $C_{10}$ cycloalkoxycarbonyloxyalkyloxy, $C_5$ to $C_{10}$ cycloalkoxycarbonyloxy, $C_7$ to $C_{11}$ aryloxycarbonyloxy, $C_8$ to $C_{12}$ aryloxycarbonyloxyalkyloxy, $C_8$ to $C_{14}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, $C_5$–$C_{10}$ alkyldioxolenonylmethoxy, aryldioxolenonylmethoxy, N-morpholinoethoxy, or $(R^{1a})_2N$-$C_1$–$C_{10}$ alkyloxy.

2. A compound of Formula I:

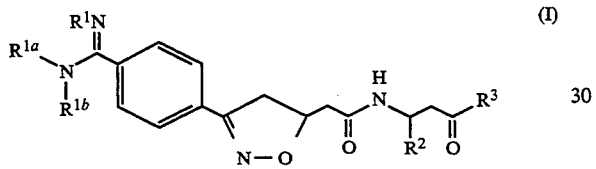

(I)

or a pharmaceutically acceptable salt form thereof wherein:

$R^1$ and $R^{1a}$ are independently selected from: H, $OR^{4a}$, $C_1$–$C_{10}$ alkyl, $C_2$–$C_6$ alkenyl, $C_3$–$C_{11}$ cycloalkyl, $C_4$–$C_{11}$ cycloalkylalkyl, $C_6$–$C_{10}$ aryl, $C_7$–$C_{14}$ arylalkyl, heteroaryl($C_1$–$C_{10}$)alkyl, $C_2$–$C_7$ alkylcarbonyl, $C_6$–$C_{10}$ arylcarbonyl, $C_2$–$C_{10}$ alkoxycarbonyl, $C_4$–$C_{11}$ cycloalkoxycarbonyl, $C_7$–$C_{14}$ bicycloalkoxycarbonyl, aryloxycarbonyl, aryl($C_1$–$C_{10}$ alkoxy)carbonyl, or heteroarylcarbonyl;

with the proviso that only one of $R^1$ or $R^{1a}$ can be $OR^{4a}$, $C_2$–$C_7$ alkylcarbonyl, arylcarbonyl, $C_2$–$C_{10}$ alkoxycarbonyl, $C_4$–$C_{11}$ cycloalkoxycarbonyl, $C_7$–$C_{14}$ bicycloalkoxycarbonyl, aryloxycarbonyl, aryl($C_1$–$C_{10}$ alkoxy)carbonyl, or heteroarylcarbonyl;

$R^{1b}$ is H, $C_1$–$C_{10}$ alkyl, $C_2$–$C_6$ alkenyl, $C_3$–$C_{11}$ cycloalkyl, OH, $OR^4$, $C_4$–$C_{11}$ cycloalkylalkyl, $C_6$–$C_{10}$ aryl, $C_7$–$C_{14}$ arylalkyl, or heteroaryl($C_1$–$C_{10}$)alkyl;

alternatively, $R^{1a}$ and $R^{1b}$ can be taken together with the nitrogen atom to which they are attached to form a 5-7 membered heterocyclic ring optionally containing 1 additional heteroatom selected from O, N or S, said heterocyclic ring being substituted with 0-2 $R^4$;

alternatively, $R^1$ and $R^{1a}$ can join to form a saturated or unsaturated carbon chain of 2-4 carbons thereby forming a 5-7 membered heterocyclic ring, said heterocyclic ring being substituted with 0-2 $R^4$;

$R^2$ is selected from H or $CH_3$;

$R^3$ is selected from: hydroxy, $C_1$ to $C_{10}$ alkyloxy, $C_3$ to $C_{11}$ cycloalkyloxy, $C_6$ to $C_{10}$ aryloxy, $C_7$ to $C_{14}$ arylalkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonyloxy, $C_7$ to $C_{11}$ aryloxycarbonyloxy, $C_8$ to $C_{12}$ aryloxycarbonyloxyalkyloxy, $C_8$ to $C_{14}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, $C_{10}$ to $C_{14}$ (5-aryl-1,3-dioxa-cyclopenten-2-one-yl)methyloxy, $C_5$–$C_{10}$ alkyldioxolenonylmethoxy, aryldioxolenonylmethoxy, N-morpholinoethoxy, or $(R^5)_2N$-$C_1$–$C_{10}$ alkyloxy;

$R^4$, when a substituent on carbon, is independently selected from: H, $C_1$–$C_4$ alkyl, aryl, or aryl($C_1$–$C_{10}$ alkyl)-;

when $R^4$ is attached to a saturated carbon atom, it may also be $=O$ or $=S$;

$R^4$, when a substituent on nitrogen, is independently selected from:

H, $C_1$–$C_4$ alkyl, aryl($C_1$–$C_{10}$ alkyl)-, $C_1$–$C_{10}$ alkoxycarbonyl, $C_1$–$C_{10}$ alkylcarbonyl, $C_1$–$C_{10}$ alkylsulfonyl, aryl($C_1$–$C_{10}$ alkyl)sulfonyl, arylsulfonyl, aryl(-$C_2$–$C_{10}$ alkenyl)sulfonyl, heteroarylsulfonyl, $C_2$–$C_4$ alkenyl, $C_4$–$C_7$ cycloalkylalkyl, $C_7$–$C_{11}$ arylalkyl, $C_7$–$C_{11}$ arylcarbonyl, $C_4$–$C_{11}$ cycloalkoxycarbonyl, $C_7$–$C_{11}$ bicycloalkoxycarbonyl, $C_7$–$C_{11}$ aryloxycarbonyl, heteroarylcarbonyl, heteroarylalkylcarbonyl, or aryl($C_1$–$C_{10}$ alkoxy)carbonyl;

$R^4$, when a substituent on sulfur, may be $=O$;

$R^{4a}$ is selected from: H, $C_1$–$C_6$ alkyl, $C_6$–$C_{10}$ aryl, $C_7$–$C_{14}$ arylalkyl, heteroaryl, heteroaryl($C_1$–$C_{10}$)alkyl, $C_3$–$C_7$ cycloalkyl, $C_4$–$C_{11}$ cycloalkylalkyl, arylcarbonyl, $C_1$–$C_{10}$ alkylcarbonyl or aryl($C_1$–$C_4$)alkylcarbonyl;

$R^5$ is independently selected from: H, $OR^{4a}$, $C_1$–$C_{10}$ alkyl, $C_2$–$C_6$ alkenyl, $C_3$–$C_{11}$ cycloalkyl, $C_4$–$C_{11}$ cycloalkylalkyl, $C_6$–$C_{10}$ aryl, $C_7$–$C_{14}$ arylalkyl heteroaryl($C_1$–$C_{10}$)alkyl, $C_2$–$C_7$ alkylcarbonyl, $C_6$–$C_{10}$ arylcarbonyl, $C_2$–$C_{10}$ alkoxycarbonyl, $C_4$–$C_{11}$ cycloalkoxycarbonyl, $C_7$–$C_{14}$ bicycloalkoxycarbonyl, aryloxycarbonyl, aryl($C_1$–$C_{10}$ alkoxy)carbonyl, or heteroarylcarbonyl;

alternatively, two $R^5$ groups can be taken together with the nitrogen atom to which they are attached to form a 5-7 membered heterocyclic ring optionally containing 1 additional heteroatom selected from O, N or S, said heterocyclic ring being substituted with 0-2 $R^4$.

3. A compound of claim 2 of Formula I, or a pharmaceutically acceptable salt form thereof, wherein:

$R^1$ is selected from H, aryl($C_1$–$C_{10}$ alkoxy)carbonyl, or $C_2$–$C_{10}$ alkoxycarbonyl;

$R^{1a}$ is selected from: H, $OR^{4a}$, $C_1$–$C_6$ alkyl, $C_2$–$C_6$ alkenyl, $C_3$–$C_{11}$ cycloalkyl, $C_4$–$C_{11}$ cycloalkylalkyl, aryl, aryl-$C_1$–$C_{10}$ alkyl, heteroaryl($C_1$–$C_{10}$)alkyl, $C_2$–$C_7$ alkylcarbonyl, arylcarbonyl, $C_2$–$C_{10}$ alkoxycarbonyl, $C_4$–$C_{11}$ cycloalkoxycarbonyl, $C_7$–$C_{14}$ bicycloalkoxycarbonyl, aryloxycarbonyl, aryl($C_1$–$C_{10}$ alkoxy)carbonyl, or heteroarylcarbonyl;

$R^{1b}$ is H;

alternately, $R^{1a}$ and $R^{1b}$ can be taken together with the nitrogen atom to which they are attached to form a 5-6 membered heterocyclic ring optionally containing 1 additional heteroatom selected from O, N or S, said heterocyclic ring being substituted with 0-2 $R^4$;

$R^2$ is selected from: H or $CH_3$;

$R^3$ is selected from: hydroxy, $C_1$–$C_{10}$ alkyloxy, aryloxy, aryl-$C_1$–$C_{10}$ alkoxy, $C_3$–$C_{10}$ alkyloxycarbonyloxyalkoxy, $C_8$–$C_{14}$ arylcarbonyloxyalkoxy, $C_5$–$C_{10}$ alkyldioxolenonylmethoxy, aryldioxolenonylmethoxy, $C_5$–$C_{10}$ cycloalkoxycarbonyloxyalkoxy, $C_5$–$C_{10}$ alkyloxyalkylcarbonyloxyalkyloxy, or N-morpholinoethoxy;

$R^4$, when a substituent on carbon, is independently selected from: H, $C_1$–$C_4$ alkyl, aryl, or aryl($C_1$–$C_{10}$ alkyl)-, or when $R^4$ is attached to a saturated carbon atom it may be =O;

$R^4$, when a substituent on nitrogen, is independently selected from: H, $C_1$–$C_4$ alkyl, aryl($C_1$–$C_{10}$ alkyl)-, $C_1$–$C_{10}$ alkoxycarbonyl, $C_1$–$C_{10}$ alkylcarbonyl, $C_4$–$C_7$ cycloalkylalkyl, $C_7$–$C_{11}$ arylcarbonyl, $C_7$–$C_{11}$ aryloxycarbonyl, or aryl($C_1$–$C_{10}$ alkoxy)carbonyl;

$R^{4a}$ is selected from: H, $C_1$–$C_6$ alkyl, $C_7$–$C_{14}$ arylalkyl, heteroaryl($C_1$–$C_{10}$)alkyl, $C_3$–$C_7$ cycloalkyl, $C_4$–$C_{11}$ cycloalkylalkyl, arylcarbonyl, $C_1$–$C_{10}$ alkylcarbonyl or aryl($C_1$–$C_4$)alkylcarbonyl.

4. A compound of claim 2 of Formula I, or a pharmaceutically acceptable salt form thereof, wherein:

$R^1$ is H;

$R^{1a}$ is selected from: H, $OR^{4a}$, $C_1$–$C_6$ alkyl, $C_4$–$C_{11}$ cycloalkylalkyl, aryl, aryl($C_1$–$C_{10}$ alkyl)-, or heteroaryl($C_1$–$C_{10}$ alkyl)-;

$R^{1b}$ is H;

alternatively, $R^{1a}$ and $R^{1b}$ can be taken together with the nitrogen atom to which they are attached to form a 5–6 membered heterocyclic ring optionally containing 1 additional heteroatom selected from O, N or S, said heterocyclic ring being substituted with 0–2 $R^4$;

$R^2$ is selected from H or $CH_3$;

$R^3$ is selected from hydroxy, $C_1$–$C_{10}$ alkyloxy, aryloxy, aryl-$C_1$–$C_{10}$ alkoxy, $C_3$–$C_{10}$ alkyloxycarbonyloxyalkoxy, $C_8$–$C_{14}$ arylcarbonyloxyalkoxy, $C_5$–$C_{10}$ alkyldioxolenonylmethoxy, aryldioxolenonylmethoxy, $C_5$–$C_{10}$ cycloalkoxycarbonyloxyalkoxy, $C_5$–$C_{10}$ alkyloxyalkylcarbonyloxyalkyloxy, or N-morpholinoethoxy;

$R^4$, when a substituent on carbon, is independently selected from: H, $C_1$–$C_4$ alkyl, or when $R^4$ is attached to a saturated carbon, it may be =O;

$R^4$, when a substituent on nitrogen, is independently selected from: H, $C_1$–$C_4$ alkyl, $C_1$–$C_{10}$ alkoxycarbonyl, $C_1$–$C_{10}$ alkylcarbonyl, $C_7$–$C_{11}$ arylcarbonyl, or aryl($C_1$–$C_{10}$ alkoxy)carbonyl;

$R^{4a}$ is selected from: H, $C_1$–$C_6$ alkyl, $C_7$–$C_{14}$ arylalkyl.

5. A compound of claim 2 of Formula I, or a pharmaceutically acceptable salt form thereof, wherein:

$R^1$ is selected from H, aryl($C_1$–$C_{10}$ alkoxy)carbonyl, or $C_2$–$C_{10}$ alkoxycarbonyl;

$R^{1a}$ is H;

$R^{1b}$ is H;

$R^2$ is selected from H or $CH_3$;

$R^3$ is selected from hydroxy, $C_1$–$C_{10}$ alkyloxy, aryloxy, aryl-$C_1$–$C_{10}$ alkoxy, $C_3$–$C_{10}$ alkyloxycarbonyloxyalkoxy, $C_8$–$C_{14}$ arylcarbonyloxyalkoxy, $C_5$–$C_{10}$ alkyldioxolenonylmethoxy, aryldioxolenonylmethoxy, $C_5$–$C_{10}$ cycloalkoxycarbonyloxyalkoxy, $C_5$–$C_{10}$ alkyloxyalkylcarbonyloxyalkyloxy, or N-morpholinoethoxy.

6. A compound of claim 2, or a pharmaceutically acceptable salt form thereof, selected from the group consisting of:

5(R,S)-3-[3-(4-amidinophenyl)isoxazolin-5-ylacetyl]aminopropanoic acid;

3(R,S)-5(R,S)-3-[3-(4-amidinophenyl)isoxazolin-5-ylacetyl]amino-3-methylpropanoic acid;

methyl 5(R,S)-3-[3-(4-N-n-butylamidinophenyl)isoxazolin-5-ylacetyl]aminopropanoate;

5(R,S)-3-[3-(4-N-n-butylamidinophenyl)isoxazolin-5-ylacetyl]aminopropanoic acid;

methyl 5(R,S)-3-[3-(4-N-propylamidinophenyl)isoxazolin-5-ylacetyl]aminopropanoate;

5(R,S)-3-[3-(4-N-propylamidinophenyl)isoxazolin-5-ylacetyl]aminopropanoic acid;

ethyl 5(R,S)-3-[3-(4-N-ethylamidinophenyl)isoxazolin-5-ylacetyl]aminopropanoate;

5(R,S)-3-[3-(4-N-ethylamidinophenyl)isoxazolin-5-ylacetyl]aminopropanoic acid;

ethyl 5(R,S)-3-[3-(4-N-methylamidinophenyl)isoxazolin-5-ylacetyl]aminopropanoate;

5(R,S)-3-[3-(4-N-methylamidinophenyl)isoxazolin-5-ylacetyl]aminopropanoic acid;

ethyl 5(R,S)-3-[3-(4-N-n-pentylamidinophenyl)isoxazolin-5-ylacetyl]aminopropanoate;

5(R,S)-3-[3-(4-N-n-pentylamidinophenyl)isoxazolin-5-ylacetyl]aminopropanoic acid;

ethyl 5(R,S)-3-[3-(4-N-isopentylamidinophenyl)isoxazolin-5-ylacetyl]aminopropanoate;

5(R,S)-3-[3-(4-N-isopentylamidinophenyl)isoxazolin-5-ylacetyl]aminopropanoic acid;

ethyl 5(R,S)-3-[3-(4-N-isobutylamidinophenyl)isoxazolin-5-ylacetyl]aminopropanoate;

5(R,S)-3-[3-(4-N-isobutylamidinophenyl)isoxazolin-5-ylacetyl]aminopropanoic acid;

ethyl 5(R,S)-3-[3-(4-N-phenethylamidinophenyl)isoxazol-5-ylacetyl]aminopropanoate;

5(R,S)-3-[3-(4-N-phenethylamidinophenyl)isoxazolin-5-ylacetyl]aminopropanoic acid;

ethyl 5(R,S)-3-[3-(4-N-pyridinylethylamidinophenyl)isoxazolin-5-ylacetyl]aminopropanoate;

5(R,S)-3-[3-(4-N-pyridinylethylamidinophenyl)isoxazolin-5-ylacetyl]aminopropanoic acid;

ethyl 5(R,S)-3-[3-(4-N-cyclohexylmethylamidinophenyl)isoxazolin-5-ylacetyl]aminopropanoate;

5(R,S)-3-[3-(4-N-cyclohexylmethylamidinophenyl)isoxazolin-5-ylacetyl]aminopropanoic acid;

methyl 5(R,S)-3-[3-(4-N-tetrahydrofuranylmethylamidinophenyl)isoxazolin-5-ylacetyl]aminopropanoate;

5(R,S)-3-[3-(4-N-tetrahydrofuranylmethylamidinophenyl)isoxazolin-5-ylacetyl]aminopropanoic acid;

ethyl 5(R,S)-3-[3-(4-N-phenylamidinophenyl)isoxazolin-5-ylacetyl]aminopropanoate;

5(R,S)-3-[3-(4-N-phenylamidinophenyl)isoxazolin-5-ylacetyl]aminopropanoic acid.

7. A method for the treatment of thromboembolic disorders which comprises administering to a host in need of such treatment a therapeautically effective amount of a compound of claim 6.

8. A pharmaceutical composition comprising therapeutically effective amount of a compound of claim 6 and a pharmaceutically effective carrier.

9. A method for the treatment of thromboembolic disorders which comprises administering to a host in need of such treatment a therapeautically effective amount of a compound of claim 2.

10. A method for the treatment of thromboembolic disorders which comprises administering to a host in need of such treatment a therapeautically effective amount of a compound of claim 3.

11. A method for the treatment of thromboembolic disorders which comprises administering to a host in need of such treatment a therapeautically effective amount of a compound of claim 4.

12. A method for the treatment of thromboembolic disorders which comprises administering to a host in need of such treatment a therapeautically effective amount of a compound of claim 5.

13. A pharmaceutical composition comprising therapeutically effective amount of a compound of claim 2 and a pharmaceutically effective carrier.

14. A pharmaceutical composition comprising therapeutically effective amount of a compound of claim 3 and a pharmaceutically effective carrier.

15. A pharmaceutical composition comprising therapeutically effective amount of a compound of claim 4 and a pharmaceutically effective carrier.

16. A pharmaceutical composition comprising therapeutically effective amount of a compound of claim 5 and a pharmaceutically effective carrier.

17. A method of inhibiting the binding of fibrinogen to blood platelets in a mammal which comprises administering to a mammal in need of such inhibition a therapeutically effective amount of a compound of claim 2.

18. A method of inhibiting the aggregation of blood platelets in a mammal which comprises administering to a mammal in need of such inhibition a therapeutically effective amount of a compound of claim 2.

19. A method of treating thrombus or embolus formation in a mammal which comprises administering to a mammal in need of such treatment a therapeutically effective amount of a compound of claim 2.

20. A method of preventing thrombus or embolus formation in a mammal which comprises administering to a mammal in need of such prevention a therapeutically effective amount of a compound of claim 2.

* * * * *